United States Patent

Tapolsky et al.

Patent Number: 6,103,266
Date of Patent: *Aug. 15, 2000

[54] PHARMACEUTICAL GEL PREPARATION APPLICABLE TO MUCOSAL SURFACES AND BODY TISSUES

[76] Inventors: Gilles H. Tapolsky, 62 S. Piney Plains, The Woodlands, Tex. 77382; David W. Osborne, 19 Quiet Oak Cir., The Woodlands, Tex. 77381

[*] Notice: This patent is subject to a terminal disclaimer.

[21] Appl. No.: 09/064,433

[22] Filed: Apr. 22, 1998

Related U.S. Application Data

[63] Continuation-in-part of application No. 08/733,454, filed as application No. PCT/US97/18606, Oct. 16, 1997, Pat. No. 5,955,097.

[51] Int. Cl.$^7$ ............................. A61K 9/14; A61K 47/00; A01N 25/00
[52] U.S. Cl. ............................................. 424/484; 514/781
[58] Field of Search ............................. 424/484; 514/781

[56] References Cited

U.S. PATENT DOCUMENTS

| | | | |
|---|---|---|---|
| 3,257,276 | 6/1966 | Broh-Kahn et al. | 514/159 |
| 3,640,741 | 2/1972 | Etes | 106/198 |
| 3,996,934 | 12/1976 | Zaffaroni | 424/148 |
| 4,226,848 | 10/1980 | Nagai et al. | 424/19 |
| 4,250,163 | 2/1981 | Nagai et al. | 424/78.05 |
| 4,285,934 | 8/1981 | Tinnell | 424/148 |
| 4,286,592 | 9/1981 | Chandrasekaran | 128/260 |
| 4,292,299 | 9/1981 | Suzuki et al. | 424/16 |
| 4,381,296 | 4/1983 | Tinnell | 424/148 |
| 4,517,173 | 5/1985 | Kizawa et al | 424/16 |
| 4,518,721 | 5/1985 | Dhabhar et al. | 523/120 |
| 4,572,832 | 2/1986 | Kigasawa et al. | 424/19 |
| 4,668,232 | 5/1987 | Cordes et al. | 604/897 |
| 4,713,243 | 12/1987 | Schiraldi et al. | 424/151 |
| 4,867,970 | 9/1989 | Newsham et al. | 424/81 |
| 4,894,232 | 1/1990 | Reul et al. | 424/439 |
| 4,900,554 | 2/1990 | Yanagibashi et al. | 424/448 |
| 4,906,463 | 3/1990 | Cleary et al. | 424/78 |
| 4,915,948 | 4/1990 | Gallopo et al. | 424/435 |
| 5,059,189 | 10/1991 | Cilento et al. | 604/307 |
| 5,081,157 | 1/1992 | Pomerantz | 514/781 |
| 5,081,158 | 1/1992 | Pomerantz | 514/781 |
| 5,137,729 | 8/1992 | Kuroya et al. | 424/435 |
| 5,166,233 | 11/1992 | Takamasa et al. | 524/37 |
| 5,192,802 | 3/1993 | Rencher | 514/535 |
| 5,298,258 | 3/1994 | Akemi et al. | 424/484 |
| 5,314,915 | 5/1994 | Rencher | 514/535 |
| 5,462,749 | 10/1995 | Rencher | 424/484 |
| 5,540,930 | 7/1996 | Guy et al. | 424/427 |
| 5,885,611 | 3/1999 | Church et al. | 424/443 |

FOREIGN PATENT DOCUMENTS 56-100714   8/1981   Japan.

*Primary Examiner*—Avis M. Davenport
*Attorney, Agent, or Firm*—Morrison & Foerster LLP

[57] ABSTRACT

The present invention relates to a non water-soluble pharmaceutical carrier gel which adheres to mucosal surfaces and body tissues upon application and forms a film, providing protection and delivery of pharmaceutical to the site of application, surrounding body tissues, and bodily fluids. The gel comprises a volatile or diffusing nonaqueous solvent and at least one non-water-soluble alkyl cellulose or hydroxyalkyl cellulose. A bioadhesive polymer may also be added. The gel provides an effective residence time with ease of use. The residence time may be adjusted by adding a component which acts to adjust the kinetics of erodability of the carrier.

37 Claims, No Drawings

PHARMACEUTICAL GEL PREPARATION APPLICABLE TO MUCOSAL SURFACES AND BODY TISSUES

The instant application is continuation-in-part application of U.S. Ser. No. 08/733,454 filed Oct. 18, 1996 now U.S. Pat. No. 5,955,097, which is a 371 of PCT/US97/18606 filed Oct. 16, 1997.

FIELD OF THE INVENTION

The present invention relates generally to pharmaceutical preparations made from film-forming water-insoluble polymers solubilized in pharmacologically compatible organic solvents, bioadhesive polymers, and an active pharmaceutical, and methods for their use. Upon application to the mucosal surface or body tissue, the preparation provides a substantive therapeutic product layer, while providing drug delivery to the treatment site.

BACKGROUND OF THE INVENTION

The localized treatment of body tissues, diseases, and wounds requires that the particular pharmaceutical component be maintained at the site of treatment for an effective period of time. Given the tendency of natural bodily fluids to rapidly wash away topically applied pharmaceutical components, the topical treatment of wet mucosal tissues has been problematic. In the mouth, saliva, natural replacement of the mucosal tissue, and eating, drinking, and speaking movements are some of the problems that have limited the effectiveness and residence time of pharmaceutical carriers.

Bioadhesive carriers are known in the art and include gels, pastes, tablets, and films. These products, however, may lack one or several of the preferred characteristics for an efficient and commercially acceptable pharmaceutical delivery device. Some characteristics which are preferred by users of bioadhesive carriers include water-erodability, ease of handling and application to the treatment site, and ease of comfort, with minimal foreign body sensation. Other preferred characteristics for an effective and user-friendly product for the treatment of mucosal surfaces include the use of pharmaceutically approved components or materials; instantaneous adhesion to mucosal surface upon application; increased residence time for the protection of the affected tissue or the delivery of the pharmaceutical component; and ease of removal of the delivery device from the affected tissue or natural dissolution of the delivery device at the delivery site.

Bioadhesive gels which are used for application to mucosal tissues and especially the oral cavity are known in the art. For example, U.S. Pat. No. 5,192,802 describes a bioadhesive teething gel made from a blend of sodium carboxymethyl cellulose and xanthan gum. The gel may also have potential use in the treatment of canker sores, fever blisters, and hemorrhoids. However, this type of pharmaceutical carrier has a very limited residence time, given that body fluids such as saliva quickly wash it away from the treatment site. Bioadhesive gels are also described in U.S. Pat. Nos. 5,314,915; 5,298,258; and 5,642,749. The gels described in those patents use an aqueous or oily medium and different types of bioadhesive and gelling agents.

Denture adhesive pastes are another type of bioadhesive product known in the art. However, these preparations are used primarily for their adhesive properties, to adhere dentures to the gums, rather than for the protection of tissue or for the topical delivery of pharmaceuticals, although drugs such as local anesthetics may be used in the paste for the relief of sore gums. U.S. Pat. Nos. 4,894,232 and 4,518,721 describe denture adhesive pastes. The '721 patent describes a combination of sodium carboxymethyl cellulose and polyethylene oxide in polyethylene glycol.

Pastes have also been used as film protectants and as drug delivery systems. One such example having film forming and adhesive properties is the product commercialized under the name Orabase®-B, which is a thick gel or paste for the relief of mouth sores. Ingredients include guar gum, sodium carboxymethyl cellulose, tragacanth gum, and pectin. Even though it does provide numbing to the area of application, the film forming behavior and bioadhesion do not last. Thus, this product has a limited residence time.

Bioadhesive tablets are described in U.S. Pat. No. 4,915,948. The water-soluble bioadhesive material used in this device is a xanthan gum or a pectin combined with an adhesion enhancing material such as a polyol. Although residence time is improved with the use of bioadhesive tablets, they are not user friendly, especially for use in the oral cavity, given the unpleasant feelings associated with their solidity, bulkiness, and slow dissolution time. Bioadhesive tablets are also described in U.S. Pat. Nos. 4,226,848; 4,292,299; and 4,250,163, and are single layer or bilayer devices having an average thickness of 0.2 to 2.5 mm. The bioadhesive tablets described in these patents utilize a non-adhesive component such as cellulose ether, a bioadhesive component such as polyacrylic acid, sodium carboxymethyl cellulose, or polyvinylpyrrolidone, and a binder for tableting purposes. The cellulose derivatives may or may not be water-soluble. The claimed cellulosic materials in the '299 patent are methyl cellulose, hydroxypropyl cellulose, and hydroxypropylmethyl cellulose.

The use of bandages or bioadhesive laminated films, which are thinner and flexible and therefore have a decreased foreign body sensation, is described in U.S. Pat. Nos. 3,996,934 and 4,286,592. These products are used to deliver drugs through the skin or mucous. The laminated films usually include an adhesive layer, a reservoir layer, and a backing layer. Bioadhesive devices designed to release drug through the skin at a given rate and over a period of time are usually not water soluble, and are not dissolved or washed away by bodily fluids.

In addition to film systems for the delivery of drug through the skin, film delivery systems for use on mucosal surfaces are also known. These types of systems, which are water-insoluble and usually in the form of laminated, extruded or composite films, are described in U.S. Pat. Nos. 4,517,173; 4,572,832; 4,713,243; 4,900,554; and 5,137,729. The '173 patent describes and claims a membrane-adhering film consisting of at least three layers, including a pharmaceutical layer, a poor water soluble layer, and an intermediate layer. The pharmaceutical layer includes the drug and a cellulose derivative selected from hydroxypropyl cellulose, methyl cellulose, and hydroxypropyl methyl cellulose. The poor water soluble layer is made by the combination of one or more cellulose derivatives with a poor water soluble fatty acid, and the intermediate layer is made of cellulose derivatives. The '832 patent relates to a soft film for buccal delivery, made by the combined use of a water soluble protein, a polyol, and a polyhydric alcohol such as cellulose and polysaccharides, and also teaches the use of coloring or flavoring agents. The '243 patent describes a single or multi-layered bioadhesive thin film made from 40–95% water soluble hydroxypropyl cellulose, 5–60% water-insoluble ethylene oxide, 0–10% water-insoluble ethyl cellulose, propyl cellulose, polyethylene, or polypropylene, and a medicament. The films are three-layered laminates and include a bioadhesive layer, a reservoir layer, and a non water-soluble outer protective layer. The '729 patent teaches a soft adhesive film applicable to the oral mucosa containing a systemic drug and comprising a mixture of a vinyl acetate non water-soluble homopolymer, an acrylic acid polymer, and a cellulose derivative. Finally, the '554 Patent describes a device for use in the oral cavity having an adhesive layer including a mixture of an acrylic acid polymer, a water-insoluble cellulose derivative, and a pharmaceutical preparation, and a water-insoluble or sparingly soluble backing layer. The adhesive layer contains the pharmaceutical, and upon application to the mucosal surface, delivers the drug.

The previous examples utilize either solid dosage forms or water soluble/aqueous media carriers. The use of non-aqueous carriers is also known. U.S. Pat. No. 4,381,296 describes a suspension of tannic acid, salicylic acid, and boric acid in ethanol. This combination is used for the treatment of herpes virus infections. Ethanol acts as the carrier and to preserve the integrity of the components, given that it is "a liquid that does not react with the components to reduce their efficacy and which does not irritate the skin". Thickener or gelling agents are not incorporated in this preparation. U.S. Pat. Nos. 5,081,157 and 5,081,158 describe compositions made of hydroxypropyl cellulose, a non-toxic volatile solvent, an esterification agent which is soluble in the solvent but not soluble in bodily fluids, water, or at body temperature, and a medicinal component. A crosslinking agent may be used. Following application and air drying, an in situ film forms. As stated in the '158 Patent, "alkyl or hydroxyalkyl substituted cellulose are not suitable substitutes for hydroxypropyl cellulose" (column 2, lines 28–31) as related to compositions and in situ methods for forming films on body tissues.

JP 56-100714 describes a preparation which comprises an uneven distribution of a medicinal layer in a coating layer by creating a tablet. The coating layer adheres to the mucosal membrane and is comprised of a cellulose ether or an acrylic acid polymer or salt. The medicinal layer comprises an ointment base comprised of water-insoluble substances such as fats and oils, waxes, hydrocarbons, higher fatty acids, higher alcohols, polyhydric alcohols or glycerol esters. A surfactant and active ingredient are also present in the medicinal layer.

SUMMARY OF THE INVENTION

The present invention relates to a non water-soluble mucoadhesive gel for application to mucosal surfaces and body tissues, utilizing volatile or diffusing solvents and non-water-soluble polymers, and carrying an active pharmaceutical component. Typically, the composition will have at least one water-insoluble alkylcellulose or hydroxyalkyl cellulose, a volatile nonaqueous solvent, and at least one active pharmaceutical. A bioadhesive polymer may also be added. Upon application, the gel forms an adhesive film, providing protection to the treatment site and delivery of pharmaceutical to the site of application, surrounding body tissues, and bodily fluids. Methods for the protection and localized delivery of pharmaceutical to mucosal surfaces or body tissues are also provided. The gel provides an is effective residence time and is easy to apply and use. If an erodable pharmaceutical carrier is desired, then a component which acts to adjust the kinetics of erodability may be added to alter the residence time.

DETAILED DESCRIPTION OF THE INVENTION

As used herein, the term "water-erodable" means that the component or carrier erodes in water-based media, such as mucosal tissues, over time. Such erosion in water may be due to factors such as dissolution, dispersion, friction, gravity, etc.

As used herein, the term "kinetics of erodability" or "erosion kinetics" refers to the timing of the release of pharmaceutical from the carrier (release profile), as well as, the timing of the erosion of the carrier itself over time (lifespan or residence time of the carrier). As described herein, kinetics of erodability are based on factors such as type and amount of components in the carrier, and additives or excipients in the carrier. In a case in which a component of the carrier is very water soluble, the kinetics of erodability of the component will closely parallel its solubility kinetics.

In the present invention, a novel non-water-soluble gel which serves as a pharmaceutical carrier, and which adheres to mucosal surfaces and body tissues, is provided. One or more pharmaceutical compounds may be incorporated in the gel. The present invention finds particular use in the localized treatment of mucosal surfaces and body tissues such as the skin. Upon application and adherence to the mucosal surface or skin, the volatile or nonaqueous solvent evaporates, diffuses, or penetrates the surrounding tissues, and a film is formed. The film offers protection to the treatment site, while also providing effective drug delivery to the treatment site, surrounding body tissues, and bodily fluids. Over time, the film erodes away.

The time for erosion is adjustable by adding a component which acts to adjust the kinetics of erodability of the carrier. Useful components are those substances which are soluble in the gel medium but dissolve in water. Often such substances are advantageously biodegradable in the presence of aqueous media or bodily fluids. In this manner, the carrier is naturally broken down and the residence time of the carrier is adjusted depending upon the desired application. Suitable components include copolymers of lactic and glycolic acids, polycaprolactone, polyorthoesters, polyphosphazene and derivatives and mixtures thereof.

The desired properties of the present invention are achieved in the combination of at least one water-insoluble, pharmacologically approved or edible alkyl cellulose or hydroxyalkyl cellulose and a volatile or nonaqueous, pharmacologically approved solvent. One or more polymers known for their bioadhesive properties may also be added to the preparation. One or more polymers know to be water-insoluble but being degraded in an aqueous medium may also be added to the preparation. Such polymers are, for example, lactide-glycolide copolymers, polycaprolactone, polyorthoesters, polyphosphazenes, cellulose acetate, vinyl acetate polymers, and polyisobutylene. The combination results in a non-water soluble gel which is capable of adhesion to mucosal tissues and skin. Thickening, coloring, flavoring, or plasticizing agents may also be used. Upon application, the solvent evaporates, diffuses, or penetrates the surrounding tissues, and a film is formed.

Unlike bioadhesive gels and pastes known in the art, which have a very limited residence time, given the tendency of bodily fluids such as saliva to wash away the gel from the treatment site, the present invention offers an increased residence time because of its filmy consistency and its nonaqueous composition. For example, the Orabase® gel is an aqueous based system, and as a result, the film formed upon application is quickly washed, away, in a matter of seconds. The nonaqueous gel described in the '296 Patent for the treatment of herpes virus infections describes a suspension of tannic acid, salicylic acid, and boric acid in ethanol. Unlike this formulation, which depends on chemical reactions of the components used, the present invention relies on a specific combination of polymers chosen for their desired adhesion and/or film-forming qualities in an appropriate solvent. Finally, the film-forming gel described in the '157 and '158 Patents, which is made of hydroxypropyl cellulose, a non-toxic volatile solvent, and an esterification agent such as salicylic acid or tannic acid, relies on the chemical reaction between its components; the present invention does not. Importantly, the '157 and '158 Patents teach away from the use of alkyl cellulose derivatives other than hydroxypropyl cellulose, stating that "the mechanism of film formation is specific to hydroxypropyl cellulose." Closely related alkyl or hydroxyalkyl-substituted cellulose, such as methyl cellulose, hydroxyethyl cellulose, and hydroxybutyl cellulose are not suitable substitutes for HPC." (column 2, lines 26–31). Despite this teaching away, the present invention indeed utilizes alkyl cellulose derivatives other than hydroxypropyl cellulose as the film-forming component(s) in a non-toxic volatile solvent, without the need for an esterification agent.

Moreover, it has been discovered that a combination of the water soluble polymer hydroxypropyl cellulose and a water insoluble alkylcellulose such as ethylcellulose may be employed in the absence of esterification agents to provide a non-water-soluble film-forming gel which serves as a pharmaceutical carrier. Such carriers comprise a gel-forming amount of a combination of alkylcellulose and hydroxypropyl cellulose in the absence of an esterification agent; a nonaqueous solvent; and a pharmaceutical. Advantageously, the characteristics of the film formed from the gel may be modified depending upon the ratio of hydroxypropyl cellulose to alkylcellulose. Such modifiable characteristics advantageously include the kinetics of erodability.

Typically, the ratio of hydroxypropyl cellulose to alkylcellulose is that necessary to form a suitable film-forming gel which serves as a pharmaceutical carrier. While this ratio may vary based on the other components, it is usually from about 16:1 to about 1:10. Typically, as the ratio of hydroxypropyl cellulose to alkylcellulose increases, the water erodability increases, i.e., the films are more readily washed away. Thus, the water soluble hydroxypropyl cellulose is a component which acts to adjust the kinetics of erodability of the carrier.

Also, unlike the bioadhesive tablets which are known in the art, which offer effective residence time but also have the disadvantages of discomfort to the user and a foreign body sensation in the oral cavity due to their solidity, bulkiness, and slow dissolution time, the present invention is a gel which offers a very limited and almost nonexistent foreign body sensation.

The residence time of the film formed upon dissipation of the solvent depends on several factors, including the amount of gel applied, as well as the components used to make the composition and their relative percentages. Use of polymers with different molecular weights or of different chemical reactivity, for example, may affect the dissolution kinetics of the film. Residence times which may be achieved with this invention range from several minutes to a day, and preferably 15 minutes to several hours, depending on the particular formulation. A desired residence time for effective drug delivery depends on the characteristics of the particular drug, but is usually from at least 20–30 minutes to about several hours. The kinetics of drug release depend on such factors as the characteristics of the carrier gel and relative percentages of its components, the total amount of pharmaceutical incorporated into the gel, the particular application site, and the physical and chemical characteristics of the particular drug or combination of drugs.

As mentioned above, the composition of the present invention includes at least one water-insoluble, pharmacologically approved, alkyl cellulose or hydroxyalkyl cellulose. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. For ethyl cellulose polymers, the preferred characteristics include an ethoxyl content between 42 and 52%, and more preferably between 44 and 50%, and for a 5% by weight of polymer in a 80/20 toluene/ethanol solution, a viscosity of between 2 and 500 cps, and more preferably between 4 and 400 cps. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

The volatile, nonaqueous pharmacologically approved solvent for use in this invention should have good penetration characteristics. Some examples include low alkyl alcohols such as methanol, ethanol, and isopropyl alcohol, ethoxydiglycol, and 1 methyl-2 pyrrolidone, volatile silicones or aerosol propellants such as fluorocarbons, dimethyl ether, hydrochlorofluorocarbon-22, 1-chloro-1,1-difluoroethane, 1,1-difluoroethane, and 1,1,1-trifluoro-2-fluoroethane, alone or in combination. The preferred solvent for use in this invention is a mixture of 10 to 50 parts 95% ethanol and 0 to 5 parts water, and more preferably 10 to 15 parts 95% ethanol and 1 to 3 parts water.

The pharmaceutical component of the present invention may comprise a single pharmaceutical or a combination of pharmaceuticals. Pharmaceuticals which may be used, either alone or in combination, include anti-inflammatory analgesic agents, steroidal anti-inflammatory agents, antihistamines, local anesthetics, bactericides and disinfectants, vasoconstrictors, hemostatics, chemotherapeutic drugs, antibiotics, keratolytics, cauterizing agents, antiviral drugs, antirheumatics, antihypertensives, bronchodilators, anticholigernics, antimenimic compounds, hormones and macromolecules, peptides, proteins and vaccines.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc. Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, etc.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc. Examples of local anesthetics include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iode, cetylpyridinium chloride, eugenol, trimethylammonium bromide, etc. Examples of vasoconstrictors include naphazoline nitrate, tetrahydrozoline hydrochloride, oxymetazoline hydrochloride, phenylephrine hydrochloride, tramazoline hydrochloride, etc. Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, etc. Examples of antibiotics include penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, cycloserine, etc.

Examples of keratolytics include salicylic acid, podophyllum resin, podolifox, and cantharidin. Examples of cauterizing agents include the chloroacetic acids and silver nitrate. Examples of antiviral drugs include protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of proteins, peptides, vaccines, genes and the like include heparin, insulin, LHRH, interferons, oligonucleotides, calcitonin, and octeotride.

Examples of other pharmaceuticals which can be employed herein include omeprazole, fluoxeline, ethinylestradio, amlodipine, paroxeline, enalapril, lisinopril, leuprolide, pravastatin, lovastatin, norethindrone, risperiodone, olanzapine, albuterol, hydrochlorothiazide, pseudoephedrine, warfarin, terazosin, cisapride, ipratroplum, buspirone, methylphenidate, lavothyroxine, zopidem, lavonorgestrel, glyburide, benazepril, medroxyprogesterone, clonazepam, ondansetron, losartan, quinapril, nitroglycerin, midazolan versed, cetirizine, doxazosin, glipizide, vaccine hepatitis B, salmeterol, sumatripian, triamcinolone aceton, goserelin, beclomethasone, granisetron, desogestrel, alprazoiam, estradiol, nicotine, interferon Beta 1A, cromclyn, fosinopril, digoxin,, fluticasone, bisoprcloi, calcitriol, captopril, butorphanol, clonidine, premarin, dinoprostone, testosterone, sumatriptan, ciotrimazole, bisacodyl, dextromethorphan, nitroglycerin in D, nafarelin, dinoprosione, nicotine, bisacodyl, salicyclic acid, clioquinol, haloprogin, miconazole nitrate, povidone-iodine, tolnaftate, undecylenic acid, calcium undecylenate, copper undecylenate, and zinc undecylenate, benzocaine, butamben picrate, dibucaine, dibucaine Hcl, dimenthisoquin HCl, dyclonine HCl, lidocaine, lidocaine HCl, pramoxine, tetracaine, tetracaine HCl, benzyl alcohol, camphor, camphorated metacresol, juniper tar, menthol, phenol, phenolate sodium, resorcinol, diphenhydramine HCl, tripelennamine HCl, hydrocortisone, hydrocortisone acetate, ally isothiocyanate, strong ammonia solutin, methyl salicylate, turpenitine oil, camphor, menthol, methyl nicotinate, capasaicin, capsicum containing capsaicin, capsicum oleoresin containing capsaicin.

In addition, one or more polymers known for their bioadhesive properties may be incorporated into the composition. The polymers should be pharmacologically approved or accepted as edible components. Use of the bioadhesive polymer strengthens the adhesive nature of the film, when adhesion has to be particularly effective for reasons due to a particular drug or drug content, the specific site of application, or specific mucosal tissues. Some polymers having bioadhesive properties for use in this invention include polyacrylic acid, cross linked or not, polyvinylpyrrolidone, and sodium carboxymethyl cellulose, alone or in combination. Additionally, if erosion of the gel is desired then a substance may be employed which is bioderodable in aqueous media or bodily fluids. Suitable substances include copolymers of lactic and glycolic acids, polycaprolactone, polyorthoesters, polyphosphazene and derivatives and mixtures thereof.

Permeation enhancers may also be used to improve absorption of the drug at the treatment site. Permeation enhancers for use in this invention include sodium lauryl sulfate, sodium glycocholate, azone, EDTA, sodium cholate, sodium 5-methoxysalicylate, and others known in the art.

The relative percentages of the component materials of the present invention may vary, depending on the type of drug or combination of drugs, the particular target treatment site, the solvent, and the particular polymers used. Preferably, the solvent or combination of solvents comprises between 50 and 80% by weight of the composition. More preferably, the solvent comprises between 60 and 70% by weight. The film forming polymer or combination of polymers preferably comprises between 4 and 20% by weight of the composition, and more preferably between 6 and 12% by weight. The active pharmaceutical or combination of pharmaceuticals comprises between 0.1 and 25% by weight, more preferably between 0.2 and 20% by weight. Optionally, a bioadhesive polymer may be used and should comprise between 0 and 10% by weight, more preferably between 1 and 8% by weight. If a biodegradable substance is employed, it typically comprises from about 0 to about 10, preferably from about 1 to about 8% by weight of the total composition. The optional flavoring, coloring, or thickening agents and/or permeation enhancer should comprise between 0 and 3% by weight, more preferably between 0.5 and 2.5% by weight.

The characteristics of the film which is formed upon application of the gel, such as thickness, tensile strength, and erosion kinetics, are not described, given that they may vary greatly depending on such factors as the properties of the tissue to which the gel is applied, the amount of gel applied, the amount of saliva or other bodily fluid at the treatment site or surrounding areas, the contact surface, and other physiological factors. Because many of these physiological factors are impossible to reproduce, the mechanical properties of a film obtained ex vivo or in vitro are very different from the ones obtained in situ and have not been characterized. However, the properties of the film obtained in vivo may be adjusted via the formulation of the gel, as well as by the addition of plasticizers, the use of cross linking agents, or the amount of solvent residual.

To make the gel of the present invention, the various components are dissolved in the chosen solvent. Because of the possibility that one or more of the components might not be in solution, a suspension may also be formed. The gelling step may take place at any moment and may be induced by, for example, the addition of a special component, a change in pH, a change in temperature, or over time. For an aerosol spray, the formulation may be a solution in the container which gels upon dispensing.

The solutions and gels may be prepared by various methods known in the art so long as the gel is substantially homogenous, i.e., the pharmaceutical is distributed substantially uniformly within the gel medium. As one skilled in the art will appreciate, if an aerosol propellant is employed then suitable pressures, percentages, and containers are required. Upon preparation, the gel may be applied to the treatment site by spraying, dipping, or direct application by finger, swab, or any type of applicator.

Methods for the treatment of mucosal surfaces and body tissues using the pharmaceutical carrier of the present invention are also provided. In one embodiment, a method for the protection and localized delivery of pharmaceutical to mucosal surfaces or body tissues comprises the steps of preparing a non-water soluble, film-forming pharmaceutical carrier having at least one water-insoluble alkyl cellulose or hydroxy alkyl cellulose, a volatile, nonaqueous solvent, and at least one active pharmaceutical component; and applying the pharmaceutical carrier to the mucosal surface or body tissue by spraying, dipping, or direct application by finger or swab. In another embodiment, the method further comprises the use of at least one polymer having bioadhesive properties in the preparation of the pharmaceutical carrier. In a preferred embodiment, the method further comprises the use of ethyl cellulose, a 95% ethanol and water mixture; polyacrylic acid; and a local anesthetic.

EXAMPLE 1

An ethyl alcohol based gel was prepared using the following components: 65% by weight 95% ethyl alcohol; 0.8% by weight mint flavor; 8% by weight ethylcellulose; 2.2% by weight polyacrylic acid; 5% water USP; 15% benzocaine USP; and 4% by weight menthol USP. A clear, yellowish gel with film-forming capabilities was formed.

EXAMPLE 2

An ethyl alcohol/ethoxydiglycol based gel was prepared using the following components: 55% by weight 95% ethyl alcohol; 1% by weight mint flavor; 8% by weight ethylcellulose; 2% by weight polyacrylic acid; 15% by weight ethoxydiglycol; 15% by weight benzocaine USP; and 4% by weight menthol USP. Here, the mixture of two compatible solvents impacted the time for the film to form. Compared to Example 1, which used a mixture of 95% ethyl alcohol and water as the solvent, the film-forming kinetics of this gel were slower.

EXAMPLE 3

An ethyl alcohol based gel was prepared using the following components: 75% by weight ethyl alcohol; 1% by weight mint flavor; 4% by weight ethylcellulose Mw with a viscosity between 8 to 12 cps in an 80/20 toluene/ethanol solution at 25° C.; 4% by weight ethylcellulose, Mw with a viscosity between 90 and 110 cps in an 80/20 toluene/ethanol solution at 25° C.; 3% polyacrylic acid; 9% by weight ethoxydiglycol; and 4% by weight dyclonine. Compared to the gel of Example 1, here, the use of two different ethylcellulose grades resulted in a gel having a stiffer and thicker consistency, which slightly increased the foreign body sensation.

EXAMPLE 4

An ethyl alcohol/1-methyl-2-pyrrolidone based gel was prepared using the following components: 55% by weight of 95% ethyl alcohol; 1.5% by weight mint flavor; 26% by weight 1-methyl-2-pyrrolidone; 6% by weight ethylcellulose; 2.5% by weight polyacrylic acid; 5% by weight water; and 4% by weight menthol USP. Because the use of methyl pyrrolidone resulted in a poor taste, a higher percentage of flavoring agent had to be used to mask the taste. Compared to the gel of Example 1, this gel had poor acceptance with users, given the taste. However, the kinetics of diffusion of this gel were appropriate and allowed for the formation of a nice film.

EXAMPLE 5

An ethyl alcohol based gel was prepared, using polyvinyl pyrrolidone as a bioadhesive polymer. The components used were as follows: 65% by weight 95% ethyl alcohol; 0.8% by weight mint flavor; 6.2% by weight ethylcellulose; 4% by weight polyvinyl pyrrolidone; 5% by weight water USP; 15% by weight benzocaine USP; and 4% by weight menthol USP. Here, the use of polyvinyl pyrrolidone instead of polyacrylic acid as the bioadhesive polymer resulted in the formation of a nice film, but adhesion seemed to be weaker than that achieved with the use of polyacrylic acid.

EXAMPLE 6

An ethyl alcohol based gel was prepared, using sodium carboxymethyl cellulose as a bioadhesive polymer. The components used were as follows: 75% by weight of 95% ethyl alcohol; 1% by weight mint flavor; 8% by weight ethylcellulose; 4% by weight sodium carboxymethyl cellulose; 8% by weight water USP; and 4% by weight menthol USP. Here, the use of sodium carboxymethyl cellulose instead of polyacrylic acid resulted in a weaker adhesion, given that sodium carboxymethyl cellulose does not dissolve as well in ethanol as polyacrylic acid does, and a partial suspension was formed, altering the adhesion characteristics of the gel.

EXAMPLE 7

An ethyl alcohol based gel was prepared using the following components: 78% by weight of 95% ethyl alcohol; 1% by weight mint flavor; 8% by weight ethylcellulose; 3% by weight polyacrylic acid; 6% by weight water USP; 0.1% by weight sodium lauryl sulfate; and 3.9% by weight dyclonine USP. Here, the gel formed was comparable to that of Example 1. However, the use of a different anesthetic, dyclonine instead of benzocaine, resulted in a less intense numbing effect.

EXAMPLE 8

A gel according to the formulation provided in example 1 was prepared and administered to eight healthy volunteers. Participants were asked to apply a very small quantity of the gel to the tip of one finger and then to place and quickly spread/rub the gel at one location in the oral cavity. The volunteers were asked to describe, on a scale of 0 to 3 (with 3 being very good, 2 good, 1 fair, and 0 poor), the ease of handling of the gel, and its numbing effect. The volunteers were also asked to describe the time necessary for the formation of a film at the site of application, as well as its residence time, and whether or not they experienced a foreign body sensation. Additionally, the volunteers were asked to describe as positive (+) or negative (−) their impressions of the taste and overall efficiency of the gel, as well as their overall impression of the gel.

The results are provided in Table 1 below.

TABLE 1

| No. | Handling | Time for film to form | Residence Time | Numbing effect | Taste | Efficiency | Foreign Body Sensation | Overall Impression |
|---|---|---|---|---|---|---|---|---|
| 1 | 3 | <30 sec | ~1 hr | 3 | + | + | minor | + |
| 2 | 2 | <1 min | ~1 hr | 2 | − | + | none | + |
| 3 | 3 | <30 sec | ~2 hr | 2 | − | + | minor | − |
| 4 | 3 | <1 min | ~2 hr | 3 | − | − | none | − |
| 5 | 3 | <1 min | ~3 hr | 2 | + | + | yes | + |
| 6 | 2 | <30 sec | ~1 hr | 2 | + | + | yes | + |
| 7 | 2 | <1 min | ~2 hr | 3 | − | + | none | − |
| 8 | 3 | <1 min | ~2 hr | 2 | + | + | minor | + |

The results demonstrate that the formulation of Example 1 is easy to apply and rapidly forms a film, while providing only a minimal foreign body sensation to the user. The film stays in place long enough to provide effective drug delivery, while also providing effective numbing to the treatment site and surrounding tissues.

EXAMPLE 9

Commercially available products Anbesol®, Orabase-B®, Oragel®, and Zilactin-B® were evaluated for their residence times and film characteristics, including their pattern of erosion and dissolution, as compared to a formulation of Example 1. Each product was spread over a ¼ inch diameter mask set on a microslide. The set of microslides were left to dry overnight at room temperature. The next day, the masks were removed, resulting in dried films. Each microslide was then placed into a beaker of distilled water at constant stirring of 300 rpm, such that the film was completely immersed.

While immersed in water, the films on the microslides were observed; the results are described in Table 2 below:

have good film-forming abilities or residence times, which may be because its components are water-soluble and not film-forming. This may explain the rapid pattern of erosion and dissolution, whereby strips of the film were observed to fall off of the slide.

Zilactin-B® showed good adhesion and residence time, probably the result of the use of film-forming materials which were transformed by crosslinking in their preparation. However, it seems that the film was slightly heterogenous, given that the erosion was slow but strips of film were observed to fall off over time. In the case of the formulation of Example 1 of the present invention, the film did not fall off in strips but rather remained a whole homogenous disk which peeled off the slide after water slowly migrated along the interface, decreasing the adhesion of the film to the glass slide.

This example is not meant to be a substitute for a measure of in vivo residence times, given that the use of water in this Example does not totally replicate the composition of bodily fluids such as saliva, and the surface of a microslide cannot replicate a mucosal surface or body tissue substrate. This

TABLE 2

| Product | Residence Time on Slide | Pattern of erosion/dissolution | Pattern of erosion/dissolution in the aqueous solution |
|---|---|---|---|
| Anbesol® | 5–10 min. | immediate erosion, taking away strips of film | fine suspension and solubilization |
| Orabase-B® | 3–4 min. | almost immediate solubilization | solution |
| Oragel® | 3–5 min. | almost immediate solubilization | solution |
| Zilactin-B® | 120–160 min. | good adhesion; no noticeable erosion prior to about 1 hr; heterogenous erosion leading to uneven losses into solution | strips of the film eventually break into smaller pieces/partial solubilization |
| formulation of Example 1 | 140–150 min. | good adhesion; erosion not noticeable; migration of water observed about 1.5 hr; film as a whole peels off and falls into the water and stays intact in the solution | the whole film stays intact in water; no appearance of solubilization or erosion in pieces |

The results demonstrate that aqueous based gels such as Orabase® and Oragel® have a tendency to readily mix with water, thus, significantly limiting their presence as a film or drug depot. Alcohol based gels such as Anbesol® do not have good film-forming abilities or residence times, which Example was designed to compare the different products in vitro. It is also important to note that the use of a microslide as a substrate provided mechanical support to the compositions, whereas in an in vivo situation, normal bodily movements and bodily fluids would probably accelerate the erosion of compositions with poor film-forming capabilities.

EXAMPLE 10

An aerosol spray is prepared by mixing 40% by weight ethanol and 40% by weight DYMEL 152A. To this solution 4% by weight ethylcellulose, 0.2% by weight oleic acid, and water are added. Upon spraying this formulation induces a film which adheres readily to skin or mucosal tissues.

EXAMPLE 11

An ethyl alcohol based gel was prepared by mixing the following components: 70% by weight of 95% ethyl alcohol; 8% by weight ethylcellulose; 2% by weight hydroxypropylcellulose; 15% by weight salicylic acid; and 5% by weight water USP. A smooth and slightly opaque gel with film-forming capabilities was formed.

EXAMPLE 12

An ethyl alcohol based gel was prepared by mixing the following components: 78.95% by weight of 95% ethyl alcohol; 8% by weight ethylcellulose; 2% by weight hydroxypropylcellulose; 2% by weight polyacrylic acid; 4% by weight menthol; 0.05% by weight capsaicin and 5% by weight water USP. A smooth, slightly opaque and sticky gel was formed.

EXAMPLE 13

An ethyl alcohol based gel was prepared by mixing the following components: 67% by weight of 95% ethyl alcohol; 8% by weight ethylcellulose; 2% by weight hydroxypropylcellulose; 2% by weight polyacrylic acid; 16% by weight menthol and 5% by weight water USP. A smooth, slightly opaque and sticky gel was formed.

EXAMPLE 14

A gel was prepared in a manner similar to Example 13 except that 2% by weight ethylcellulose and 8% by weight hydroxypropylcellulose were employed instead of 8% by weight ethylcellulose and 2% by weight hydroxypropylcellulose.

EXAMPLE 15

A gel was prepared in a manner similar to Example 13 except that 1% by weight ethylcellulose and 9% by weight hydroxypropylcellulose were employed instead of 8% by eight ethylcellulose and 2% by weight hydroxypropylcellulose.

EXAMPLE 16

A gel was prepared in a manner similar to Example 13 except that 0.5% by weight ethylcellulose and 9.5% by weight hydroxypropylcellulose were employed instead of 8% by weight ethylcellulose and 2% by weight hydroxypropylcellulose.

COMPARISON OF EXAMPLES 13–16

The films, resulting from the application of a dab of gels described in examples 13–16, are nice, cohesive, protective films that have different water erodability behavior. For instance, while the films obtained with gels from example 15 and 16 may be washed away, a film obtained with the gel from example 14 does not wash away as quickly and, finally, a film resulting from the gel described in example 13 usually has to be scrubbed off.

Those skilled in the art will recognize that, while specific embodiments have been illustrated and described, various modifications and changes may be made without departing from the spirit and scope of the invention.

We claim:

1. A non-water soluble, film-forming gel which adheres to mucosal surfaces and body tissues and forms a pharmaceutical carrier to provide localized delivery of a pharmaceutical to a treatment site, said gel comprising a water-insoluble alkyl cellulose or water-insoluble hydroxyalkyl cellulose; a pharmacologically acceptable solvent; and a pharmaceutical.

2. The gel of claim 1, further comprising a polymer having bioadhesive properties.

3. The gel of claim 1, wherein said water-insoluble alkyl cellulose or water-insoluble hydroxyalkyl cellulose comprises ethyl cellulose, propyl cellulose, butyl cellulose, cellulose acetate, hydroxybutyl cellulose, ethylhydroxyethyl cellulose, or a combination thereof.

4. The gel of claim 1, wherein said solvent comprises methanol, ethanol, isopropyl alcohol, ethoxydiglycol, 1-methyl-2-pyrrolidone, volatile silicones, fluorocarbons, dimethyl ether, hydrochlorofluorocarbon-22, 1-chloro-1,1-difluoroethane, 1,1-difluoroethane, 1,1,1-trifluoro-2-fluoroethane, or a combination thereof.

5. The gel of claim 1, wherein said solvent comprises a mixture of 10 to 50 parts 95% ethanol and 0 to 5 parts water.

6. The gel of claim 2, wherein said polymer having bioadhesive properties comprises polyacrylic acid, polyvinylpyrrolidone, sodium carboxymethyl cellulose, copolymers of lactic and glycolic acids, polycaprolactone, polyorthoesters, polyphosphazene, cellulose acetate, polyvinyl acetate, polyisobutylene, or a combination thereof.

7. The gel of claim 1, further comprising a permeation enhancer.

8. The gel of claim 1, wherein said pharmaceutical comprises an anti-inflammatory analgesic agent, a steroidal anti-inflammatory agent, an antihistamine, a local anesthetic, a bactericide, a disinfectant, a vasoconstrictor, a hemostatic, a chemotherapeutic drug, an antibiotic, a keratolytic, a cauterizing agent, an antiviral drug, an antirheumatic, an antihypertensive, a bronchodilator, an anticholigernic, an antimenimic compounds, an hormone, a macromolecule, a peptide, a protein, a vaccine, or a combination thereof.

9. The gel of claim 1, further comprising a component which acts to adjust the kinetics of erodability of the pharmaceutical carrier.

10. The gel of claim 9, wherein the component which acts to adjust the kinetics of erodability of the pharmaceutical carrier comprises a water soluble polymer, copolymers of lactic and glycolic acids, polycaprolactone, polyorthoesters, polyphosphazene, and mixtures thereof.

11. A non-water soluble gel which adheres to mucosal surfaces or body tissues upon application and forms a film which serves as a pharmaceutical carrier for the localized delivery of pharmaceutical, said gel comprising ethylcellulose, ethanol, polyacrylic acid, and a pharmaceutical.

12. The gel of claim 11, wherein said ethylcellulose comprises 4 to 20% by weight of the composition, said ethanol comprises 50 to 80% by weight of the composition, said polyacrylic acid comprises 0 to 10% by weight of the composition, and said pharmaceutical comprises 0.1 to 25% by weight of the composition.

13. The gel of claim 11, wherein said pharmaceutical comprises an anti-inflammatory analgesic agent, a steroidal anti-inflammatory agent, an antihistamine, a local anesthetic, a bactericide, a disinfectant, a vasoconstrictor, a hemostatic, a chemotherapeutic drug, an antibiotic, a keratolytic, a cauterizing agent, a retroviral drug, or a combination thereof.

14. The gel of claim 11, further comprising a component which acts to adjust the kinetics of erodability of the pharmaceutical carrier.

15. The gel of claim 14, wherein the component which acts to adjust the kinetics of erodability of the pharmaceutical carrier comprises a water soluble polymer, copolymers of lactic and glycolic acids, polycaprolactone, polyorthoesters, polyphosphazene cellulose acetate, polyvinyl acetate, polyisobutylene, and mixtures thereof.

16. A non-water soluble, film-forming gel which adheres to mucosal surfaces and body tissues and forms a pharmaceutical carrier to provide localized delivery of pharmaceutical to a treatment site, said gel comprising a water-insoluble alkyl cellulose or hydroxyalkyl cellulose; a pharmacologically acceptable solvent; a polymer having bioadhesive properties selected from the group consisting of polyacrylic acid, polyvinylpyrrolidone, and sodium carboxymethyl cellulose; and a pharmaceutical.

17. The gel of claim 16, wherein said water-insoluble alkyl cellulose or water-insoluble hydroxyalkyl cellulose comprises ethyl cellulose, propyl cellulose, butyl cellulose, cellulose acetate, hydroxybutyl cellulose, ethylhydroxyethyl cellulose, or a combination thereof.

18. The gel of claim 16, wherein said solvent comprises methanol, ethanol, isopropyl alcohol, ethoxydiglycol, 1-methyl-2-pyrrolidone, volatile silicones, fluorocarbons, dimethyl ether, hydrochlorofluorocarbon-22, 1-chloro-1,1-difluoroethane, 1,1-difluoroethane, 1,1,1-trifluoro-2-fluoroethane, or a combination thereof.

19. The gel of claim 16, wherein said solvent comprises a mixture of 10 to 50 parts 95% ethanol and 0 to 5 parts water.

20. The gel of claim 16, wherein said pharmaceutical comprises an anti-inflammatory analgesic agent, a steroidal anti-inflammatory agent, an antihistamine, a local anesthetic, a bactericide, a disinfectant, a vasoconstrictor, a hemostatic, a chemotherapeutic drug, an antibiotic, a keratolytic, a cauterizing agent, a retroviral drug, or a combination thereof.

21. A method for the protection and localized delivery of pharmaceutical to mucosal surfaces or body tissues, comprising: forming a pharmaceutical carrier on said mucosal surfaces or body tissues by applying a non-water soluble, film-forming gel to said mucosal surfaces or body tissues by spraying, dipping, or direct application by finger or swab, wherein said gel comprises a water-insoluble alkyl cellulose or hydroxyalkyl cellulose; a pharmacologically acceptable solvent; and a pharmaceutical.

22. The method of claim 21, wherein said gel further comprises a polymer having bioadhesive properties.

23. The method of claim 22, wherein said alkyl cellulose comprises ethyl cellulose; said pharmacologically acceptable solvent comprises a 95% ethanol and water mixture; said polymer having bioadhesive properties comprises polyacrylic acid; and said pharmaceutical comprises a local anesthetic.

24. The method of claim 21, wherein said gel further comprises a component which acts to adjust the kinetics of erodability of the pharmaceutical carrier.

25. The method of claim 24, wherein the component which acts to adjust the kinetics of erodability of the pharmaceutical carrier comprises a water soluble polymer, copolymers of lactic and glycolic acids, polycaprolactone, polyorthoesters, polyphosphazene, and mixtures thereof.

26. A non-water soluble, film-forming gel which adheres to mucosal surfaces and body tissues and forms a pharmaceutical carrier to provide localized delivery of pharmaceutical to a treatment site, said gel comprising a gel-forming amount of a combination of a water insoluble alkylcellulose and water soluble hydroxypropyl cellulose in the absence of an esterification agent; a pharmacologically acceptable solvent; and a pharmaceutical.

27. The gel of claim 26 wherein the ratio of hydroxypropyl cellulose to alkylcellulose is from about 16:1 to about 1:10.

28. The gel of claim 27 wherein the water insoluble alkylcellulose comprises ethylcellulose.

29. The gel of claim 28 which comprises from about 0.25 to about 15% by weight of the combination of ethylcellulose and hydroxypropylcellulose; an alcohol; and a pharmaceutical.

30. The gel of claim 29 wherein the alcohol is ethyl alcohol.

31. The gel of claim 30 which further comprises polyacrylic acid and water.

32. The gel of claim 9 wherein said component comprises a substance which dissolves or degrades in the presence of aqueous media or body fluids.

33. The gel of claim 14 wherein said component comprises a substance which dissolves or degrades in the presence of aqueous media or body fluids.

34. The method of claim 24 wherein said component comprises a substance which dissolves or degrades in the presence of aqueous media or body fluids.

35. The gel of claim 9, wherein said component which acts to adjust the kinetics of erodability of the pharmaceutical carrier is hydroxypropyl cellulose.

36. The gel of claim 14, wherein said component which acts to adjust the kinetics of erodability of the pharmaceutical carrier is hydroxypropyl cellulose.

37. The method of claim 24, wherein said component which acts to adjust the kinetics of erodability of the pharmaceutical carrier is hydroxypropyl cellulose.

* * * * *